United States Patent [19]

Denick, Jr.

[11] Patent Number: 4,978,529

[45] Date of Patent: Dec. 18, 1990

[54] EASILY DISPERSIBLE PSYLLIUM COMPOSITIONS

[76] Inventor: John Denick, Jr., R.D. 7, Box 372, Newton, N.J. 07860

[21] Appl. No.: 198,256

[22] Filed: May 25, 1988

[51] Int. Cl.$^5$ .............................................. A61K 35/78
[52] U.S. Cl. ................................... 424/195.1; 514/57; 514/892
[58] Field of Search .............. 424/195.1; 514/57, 89 Z

[56] References Cited

U.S. PATENT DOCUMENTS

| | | | |
|---|---|---|---|
| 4,089,981 | 5/1978 | Richardson | 426/574 X |
| 4,156,021 | 5/1979 | Richardson | 426/574 X |
| 4,321,263 | 3/1982 | Powell et al. | 424/195.1 |
| 4,459,280 | 7/1984 | Colliopoulos et al. | 514/778 X |
| 4,551,331 | 11/1985 | Rudin | 424/195.1 |
| 4,824,672 | 4/1989 | Day et al. | 424/195.1 |
| 4,828,842 | 5/1989 | Furst et al. | 424/195.1 X |

OTHER PUBLICATIONS

*The Condensed Chemical Dictionary,* Tenth Edition, pp. 697, 957 (1981).
*The Merck Index, Tenth Edition,* pp. 1095,1130 (1983).

Primary Examiner—John W. Rollins

[57] ABSTRACT

Powdered psyllium seek husks are rendered rapidly and uniformly dispersible in water by admixing a solvent selected from the group consisting of benzyl alcohol, propylene glycol, triacetin and mixtures thereof with powdered psyllium seed husks.

5 Claims, No Drawings

EASILY DISPERSIBLE PSYLLIUM COMPOSITIONS

FIELD OF THE INVENTION

This invention relates to powdered psyllium seed husk compositions having improved water dispersibility. Water dispersions of psyllium compositions form a mucilaginous mass and are used as bulk laxatives. Psyllium husk is the cleaned, dried seed coat of plantago ovata forskal.

BACKGROUND OF THE INVENTION

Scienific literature is replace with the physiological effects and benefits of dietary fiber in the diet. Among those benefits are included bowel normalization, prevention of various colonic diseases such as diverticulosis, therapeutic treatment for diabetes, hypoglycemia, hypercholesterolemia, hypertriglyceridemia and respiratory diseases as well as a control for metabolic rates to help prevent obesity.

Psyllium seed husk is a well known source of dietary fiber. The single adult dose is about 3 grams of powdered psyllium seed husk which is administered by dispersing in water or an aqueous beverage. Powdered psyllium seek husk inherently has very poor wetting capabilities and therefore must be vigorously mixed with aqueous fluids to produce a palatable dispersion.

Psyllium hydrophilic mucilloid consists of the mucillaginous portion (the husk milled or unmilled) of blond psyllium seeds. Psyllium hydrophilic mucilloid contains natural mucillate and forms a gelatinous mass on contact with water. It is useful in the treatment of constipation by acting as a fecal softener and also as a demulcent in the presence of inflamed mucosa. Psyllium hydrophilic mucilloid, however, exhibits poor dispersibility and mixability in water. The numerous individual particles tend to agglomerate when psyllium hydrophilic mucilloid is mixed with water. Hydration takes place over the surface of such agglomerated aggregates to form gel-coated lumps, the interiors of which are still substantially dry, and these lumps are extremely difficult to disperse. This effect is aggravated by the fact that psyllium has a tendency to float on the surface of water, allowing partially dissolved particles to agglomerate into large masses.

Traditionally psyllium seed preparations have been formulated to contain equal parts powdered psyllium husks and a water soluble diluent such as a sugar, typically sucrose, fructose and dextrose. The high concentration of diluent aids dispersion and hydration of the powdered psyllium. The 50:50 mixtures with diluent still require vigorous agitation, reduce the available bulk laxative by half, add calories and cannot be used by those on restrictive, low calorie or sugar free diets.

Effervescent psyllium powder formulas have been developed to improve dispersion. Effervescent products are high in sodium ion and/or potassium ion content which prevent their use by individuals on a low sodium diet such as diabetics and hypertensives. In addition, the amount of bulk laxative present is only about 50%.

Various attempts have been made to overcome the poor mixing and dispersion properties of powdered psyllium.

U.S. Pat. No. 4,321,263 discloses an ingestible granulated psyllium composition consisting essentially of granules of psyllium powder having at least 90% psyllium content, which is rendered rapidly dispersible in water by the presence on the surface of the psyllium particles of a coating of an amount up to about 10% by weight of a non-toxic, normally solid, alcohol soluble, water dispersible polyethylene glycol, polyvinylpyrrolidone, or mixture thereof, effective to render the psyllium particles substantially instantly and uniformly dispersible in water.

The psyllium particles are coated by the additional step of wet granulating with the normally solid dispersant polyethylene glycol and or polyvinylpyrrolidone in a volatile organic solvent. This apparently entraps air in the granules thus permitting rapid wetting and hydration of the psyllium particles.

U.S. Pat. No. 4,459,280 discloses a method of increasing the dispersibility and mixability of psyllium hydrophilic mucilloid by applying a film of hydrolyzed starch oligosaccharide, a mono- or di- saccharide, a polyglucose, or a polymaltose.

U.S. Pat. No. 4,551,331 discloses a modified dry dietary fiber product which is readily dispersible in liquids such as water, comprising a dry dietary fiber product coated with from 0.05 to 20% by weight of the food grade emulsifier. The process for producing coated dietary fiber products comprises blending these dietary fiber product materials with the mixture of a non-toxic solvent in a food grade emulsifier followed by removing the solvent.

SUMMARY OF THE INVENTION

It has unexpectedly been discovered that a psyllium composition which wets and hydrates rapidly when mixed with water is formed by admixing an effective amount of a liquid solvent selected from the group consisting of benzyl alcohol, propylene glycol, triacetin and mixtures thereof with powdered psyllium seed husks.

DETAILED DISCUSSION

The powdered psyllium seed husks useful in the present invention are conventional powders used in commerce as such and to produce the granulated compositions described above. Psyllium seed husk is described in USP XXI at page 915 as the cleaned, dried seed coat (epidermis) separated by winnowing and thrashing from the seeds of Plantago ovata Forskal, known in commerce as Blond Psyllium or Indian Psyllium or Ispaghula, or from Plantago psyllium Linne or from Plantago indica Linne (Plantago arenaria Waldstein et Kitaibel) known in commerce as Spanish or French Psyllium (Fam. Plantaginaceae), in whole or in powdered form. The powdered form of psyllium husk is useful in the present invention.

The solvents employed in this invention are non-toxic liquids under ambient conditions and water soluble Solvents useful in the present invention are selected from the group consisting of benzyl alcohol, propylene glycol, triacetin and mixtures thereof. The solvent is present in an amount effective to cause the psyllium powder to rapidly and uniformly disperse in water and hydrate.

The solvents of the present invention are monomeric. Generally, the solvent is present from about 0.1% to about 12%, preferably from about 0.2% to about 5% and most preferably from about 0.3% to about 3% by weight of the total composition. Solvent content of less than about 0.1% will not cause complete dispersion of the powdered psyllium resulting in lump formation when the composition is added to water. Solvent content of more than about 12% results in a wet composition with poor esthetic properties. Powdered psyllium compositions having a solvent content of about 0.1% to about 12% are free flowing powders which rapidly disperse then hydrate when added to water or an equivalent water containing beverage such as carbonated beverages, fruit juices, coffee, tea or other liquid.

While the invention is not to be limited to theoretical considerations, it is believed that the solvents useful in the present invention act as emulsifiers. The solvent molecules act as a bridge at the liquid solid interface between the polar water molecules and the hydrophobic portions of the mucilaginous components of powdered psyllium seed husks. This bridging facilitates rapid dispersion and then hydration of the powdered psyllium seed husks thus avoiding rapid surface hydration before complete dispersion which leads to the formation of lumps.

The compositions of the present invention are prepared by admixing the solvent with the powdered psyllium seed husks at ambient conditions until a uniform blend is formed.

The powdered psyllium compositions of the present invention may contain one or more conventional adjunct materials such as but not limited to flavorants artificial and natural sweeteners, colorants, preservatives and dietary fiber. When present, adjunct materials may be added to the powdered psyllium seed husks before or after addition of the solvent.

The adjunct materials when present are added in sufficient amount for their intended purpose. The determination of such an amount would generally be obvious to one skilled in the art.

Dietary fiber when present is used as a filler or bulking agent in amounts up to about 25% by weight of the present invention though larger amounts could be used. Generally, for purposes of the present invention the term "dietary fiber" is intended to mean any food which when ingested in a monogastric animal, especially a human, reaches the large intestine essentially unchanged. In essence, dietary fiber is understood to mean those constituents derived from botanical materials which are resistant to human digestive enzymes. The term "dietary fiber complex" is, for purposes of this invention, to be used interchangeably with the term dietary fiber the former providing a larger definitional umbrella for products such as microbial and algal gums which are also resistant to animal digestive enzymes. Although these materials bear little resemblance to a true fibrous material, they have in common with the true fiber, digestive resistance and serve as microbial substrates or contribute to unfermented and undigested matter of the feces.

Dietary fiber is more particularly defined as the sum of all polysaccharides and lignin that are not digested by the endogenous secretions of the human digestive tract. The polysaccharides are derived from either the plant cell-wall or cell-content. Those carbohydrates which are contained in the plant cell-wall include gums, mucilages, pectins, pectin substances, algal polysaccharides and hemicelluloses. All of these carbohydrate materials are classified as polysaccharides. Thus, for purposes of this invention, dietary fiber includes the above polysaccharides in addition to cellulose and lignin, individually or in combination, derived from one or more plant varieties or species.

Although the term "fiber" commonly is used to refer to filamentous string-like materials, dietary fiber is generally gelatinous or mucilaginous in character.

While psyllium seek husks are a dietary fiber for the purposes of this invention the term "dietary fiber" will refer to all dietary fibers other than psyllium seed husks.

The present invention is further illustrated by the following examples. All parts and percentages in the examples and throughout the specification and claims are by weight unless otherwise indicated.

EXAMPLE 1

Inventive Run 1

This example demonstrates the formation of product of the invention.

10 g of benzyl alcohol was added to 704 g of powdered psyllium seek husk. The mixture was mixed for 10 minutes to uniformly disperse the benzyl alcohol. This composition contains 1.41% benzyl alcohol.

3.55 g (equal to 3.5 g of powdered psyllium seek husk) of the inventive composition was added to 175 ml of tap water. The powder instantly wet and then dispersed in the water in about 15 seconds without stirring.

3.5 g of powdered psyllium seek husk was added to 175 ml of tap water. After 5 minutes the powder was floating on the surface of the water. The bulk of the powder had not wet or dispersed.

EXAMPLE 2

Inventive Runs 2 to 8 Comparative Runs A and B

This examples compares the dispersion and hydration properties of inventive Runs 2 to 8 with comparative Runs A and B.

| Ingredient/Run | Weight % of Ingredient | | | | | | | | |
|---|---|---|---|---|---|---|---|---|---|
| | 2 | 3 | 4 | 5 | 6 | 7 | 8 | A | B |
| Powdered psyllium seek husk | 84.8 | 84.3 | 84.3 | 84.3 | 84.6 | 74.2 | 83.7 | 100 | 84.85 |
| Benzyl alcohol | 0.1 | 0.6 | 0.3 | — | 0.3 | 10.7 | — | — | — |
| Propylene glycol | — | — | 0.3 | 0.6 | — | — | — | — | — |
| Triacetin | — | — | — | — | — | — | 1.2 | — | — |
| Microcrystalline cellulose | 14.1 | 14.1 | 14.1 | 14.1 | 14.1 | 14.1 | 14.1 | — | 14.1 |
| Flavorant | 1 | 1 | 1 | 1 | 1 | 1 | 1 | — | 1 |

Procedure: 2520 g of powdered psyllium seek husk were admixed with 420 g of microcrystalline cellulose and 29 g of flavorant for 10 minutes in a suitable mixer to form a blend. To 100 g portions of this blend the indicated amounts of solvents were added to form Runs 2 to 8 and B.

Test Procedure: Add 3.5 g of test mixture to 400 ml of tap water and stir gently. Read the time it takes to disperse the powder.

Result: Runs 2 to 8 disperse in less than 15 seconds. Runs A and B take more than 120 seconds to disperse.

The invention being thus described, it will be obvious that the same may be varied in many ways. Such variations are not to be regarded as a departure from the spirit and scope of the invention and all such modifications are intended to be included within the scope of the following claims.

What is claimed is:

1. An ingestible powdered psyllium composition comprising powdered psyllium seed husks and a solvent selected from the group consisting of benzyl alcohol, propylene glycol, triacetin and mixtures thereof, wherein the solvent is uniformly distributed in the powdered psyllium seed husks and present in an amount from about 0.1% to about 12% by weight of said composition, said amount being effective to cause the powdered psysslium seed husks to rapidly and uniformly disperse in water.

2. The composition of claim 1 further comprising up to about 25% of a dietary fiber other than psyllium seed husks.

3. The composition of claim 1 further comprising up to about 25% a cellulose derivative.

4. The composition of claim 1 wherein the solvent is present in an amount of about 0.2% to about 5.0% by weight of the composition.

5. A method for rendering edible psyllium powder rapidly and uniformly dispersible in water which comprises admixing a solvent selected from the group consisting of benzyl alcohol, propylene glycol, triacetin and mixtures thereof with powdered psyllium seed husks, said solvent being present in an amount from about 0.1% to about 12% by weight of said composition, said amount being effective to cause the powdered psyllium seed husks to rapidly and uniformly disperse in water.

* * * * *